United States Patent

Nishida et al.

[11] Patent Number: 5,736,632
[45] Date of Patent: Apr. 7, 1998

[54] APPARATUS FOR MEASURING AIR PERMEABILITY OF MOLDING SAND

[75] Inventors: Tadashi Nishida, Toyokawa; Kunio Asakura, Toyohashi, both of Japan

[73] Assignee: Sintokogio, Ltd., Nagoya, Japan

[21] Appl. No.: 639,356

[22] Filed: Apr. 26, 1996

[30] Foreign Application Priority Data

Apr. 28, 1995 [JP] Japan .................. 7-129493

[51] Int. Cl.$^6$ .................. G01N 15/08; G01N 33/24
[52] U.S. Cl. .................. 73/38
[58] Field of Search .................. 73/38

[56] References Cited

U.S. PATENT DOCUMENTS

| | | | |
|---|---|---|---|
| 4,715,212 | 12/1987 | Johanson | 73/38 |
| 4,891,967 | 1/1990 | Vogt | 73/38 |

FOREIGN PATENT DOCUMENTS

| | | | |
|---|---|---|---|
| 1-15825 | 3/1989 | Japan . | |
| 1-76710 | 12/1991 | Japan . | |
| 652266 | 3/1979 | U.S.S.R. | 73/38 |

*Primary Examiner*—Michael Brock
*Assistant Examiner*—Daniel S. Larkin
*Attorney, Agent, or Firm*—Limbach & Limbach L.L.P.

[57] ABSTRACT

An apparatus is disclosed to measure with accuracy and stability the permeability of molding sand that is compacted, by directly applying compressed air to the compacted molding sand such that the air circulates through the molding sand. The apparatus includes a hollow testing cylinder (1) having upper and lower ends that are open, the lower end being tapered such that the inner diameter of the lower open end is smaller than that of the upper open end, a squeezing head (4) horizontally movable to close the upper open end of the hollow testing cylinder, a pressing body (3) disposed in the cylinder such that the body slides in the hollow testing cylinder, the body having a sealing (5) attached to the circumferential part of its lower end, a cylinder (2) disposed below the testing cylinder, the cylinder (2) having a pressing rod (2a) connected to the pressing body (3), an air take-in aperture (6) formed in the side wall of the hollow testing cylinder at a position above the pressing body when the pressing body is situated at the lower open end, and a detecting aperture (7) formed in the side wall of the hollow testing cylinder at a position above the pressing body when the pressing body is situated at the lower open end.

4 Claims, 2 Drawing Sheets

APPARATUS FOR MEASURING AIR PERMEABILITY OF MOLDING SAND

FIELD OF THE INVENTION

This invention relates to an apparatus for automatically measuring the air permeability of molding sand by supplying an air flow to a testing cylinder after the molding sand is compacted in the testing cylinder.

DESCRIPTION OF THE PRIOR ART

Conventionally, devices disclosed in, for example, Japanese Patent (B) 1-15825 and Japanese Patent (B) 3-76710 are used to automatically measure the air permeability of molding sand. However, since each of these devices uses a method for cycling the molding sand through a pressing body that has a vent hole and that compacts the molding sand, the air permeability of the molding sand itself is not measured accurately. In other words, for good compaction by the pressing body, the body must be provided with small slits for the vent hole. However, gains of sand tend to clog in the slits and impair the passage of air through them when the molding sand is pressed and compacted. This results in a drawback in that a measuring error is caused.

This invention aims to resolve this drawback. It aims to provide an apparatus for accurately measuring the air permeability of molding sand.

SUMMARY OF THE INVENTION

To the above end, the apparatus of this invention measures air permeability of molding sand includes a hollow testing cylinder having upper and lower ends that are open, the lower end being tapered such that the inner diameter of the lower open end is smaller than that of the upper open end, a squeezing head horizontally movable to close the upper open end of the hollow testing cylinder, a pressing body disposed in the cylinder such that the body slides in the hollow testing cylinder, the body having a sealing attached to the circumferential part of its lower end, a cylinder disposed below the testing cylinder, the cylinder having a pressing rod connected to the pressing body, an air take-in aperture formed in the side wall of the hollow testing cylinder at a position above the pressing body when the pressing body is situated at the lower open end, and a detecting aperture formed in the side wall of the hollow testing cylinder at a position above the pressing body when the pressing body is situated at the lower open end.

DESCRIPTION OF THE PREFERRED EMBODIMENT

Figure 1:
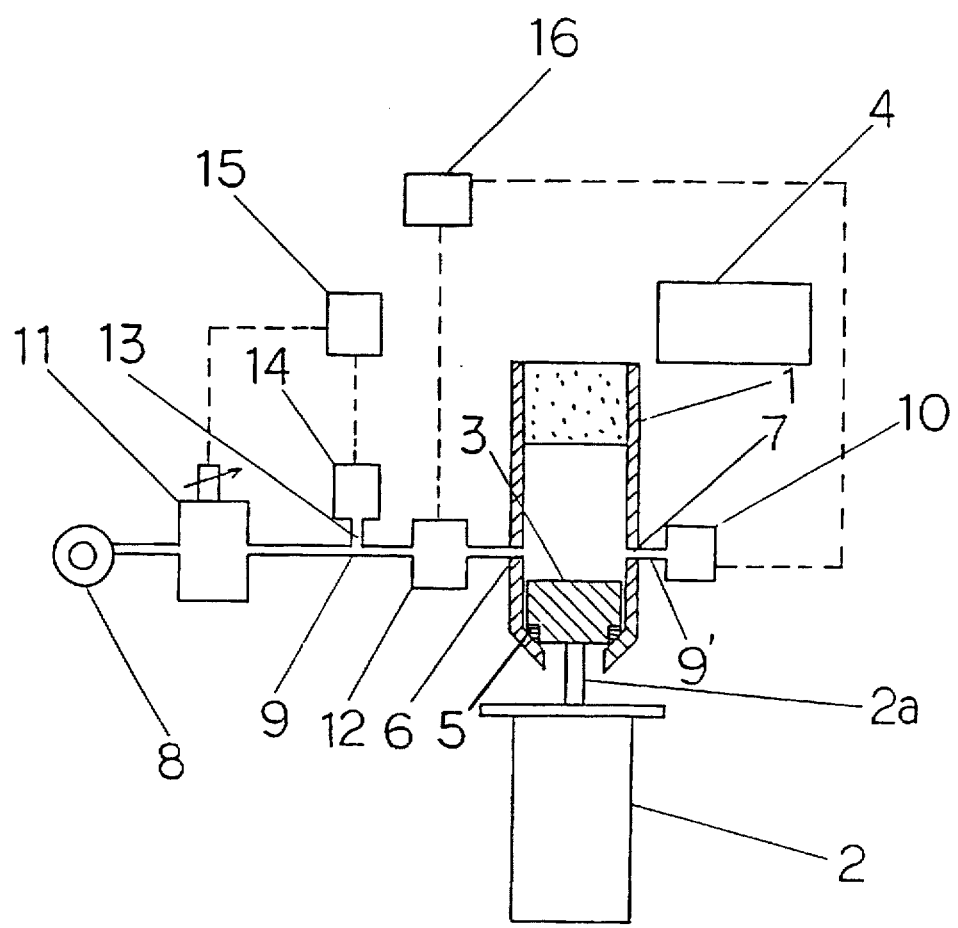
FIG. 1 is a schematic view of the device of the present invention to measure the permeability of molding sand. It shows the time at which the permeability is detected.

The invention will now be explained in detail through the embodiment. In FIG. 1 a hollow testing cylinder 1 has a lower tapered end. The inner diameter of the tapered end is smaller than that of the upper end of the testing cylinder. An electric cylinder 2 is fixedly supported by a member (not shown) below the testing cylinder 1. A pressing body 3 is disposed in the testing cylinder such that the body 3 vertically slides in it. An elastic sealing 5 is attached to the lower and circumferential part of file pressing body. The diameter of tiffs sealing part of the pressing body is slightly larger than that of the inner diameter of the straight part of the testing cylinder. A squeezing head 4 is supported above the testing cylinder by a member (not shown) such that the squeezing head is horizontally movable to close the upper open end of the testing cylinder.

Further, an air take-in aperture 6 is formed in the side wall of the testing cylinder. The aperture 6 is located above the pressing body 3 and provides communication between the outside and inside of the testing cylinder 1 when the pressing body 3 is situated at the lower open end of the testing cylinder 1. A detecting aperture 7 is formed in the side wall of the testing cylinder at a position that is symmetrical, with respect the center line of the testing cylinder, to the position where the air take-in aperture is situated. The air take-in aperture communicates with a compressed air supply source 8 through a pipe 9 so that compressed air is supplied to the testing cylinder. The detecting aperture 7 communicates with a first pressure sensor 10 through a pipe 9' so that it can detect the pressure of the compressed air taken into the testing cylinder 1. Although in the embodiment shown in the drawings both the air take-in aperture and detecting aperture are formed so as to be perpendicular to the testing cylinder, preferably these apertures may be formed to slant down from the outside to the inside of the testing cylinder such that the sand that once entered them drops due to gravity.

Between the upstream compressed air supply source 8 and the downstream aperture 6 an electro pneumatic operated proportional valve 11 and a flow sensor 12 are connected to the pipe 9. The pipe 9 communicates with a second pressure sensor 14 between the electro pneumatic operated proportional valve 11 and the flow sensor 12 through a branch pipe 13, and the second pressure sensor 14 is electrically connected to the electro pneumatic operated proportional valve 11 through a pneumatic-electro converter 15. The second pressure sensor 14 detects any variation m the pressure of the air that flows in the pipe 9, and based on the detected variation the degree that the electro pneumatic operated proportional valve 11 is opened is adjusted to maintain a predetermined pressure of the air that flows downstream to the flow sensor 12. The first pressure sensor 10 and the flow sensor 12 are electrically connected to a processor 16. The processor 16 calculates the air permeability of molding sand by using a previously stored calculation equation based on the measurements obtained by the sensors 10 and 12 and the height of the compacted molding sand which is measured by an encoder (not shown) disposed in the electric cylinder 2.

Figure 2:
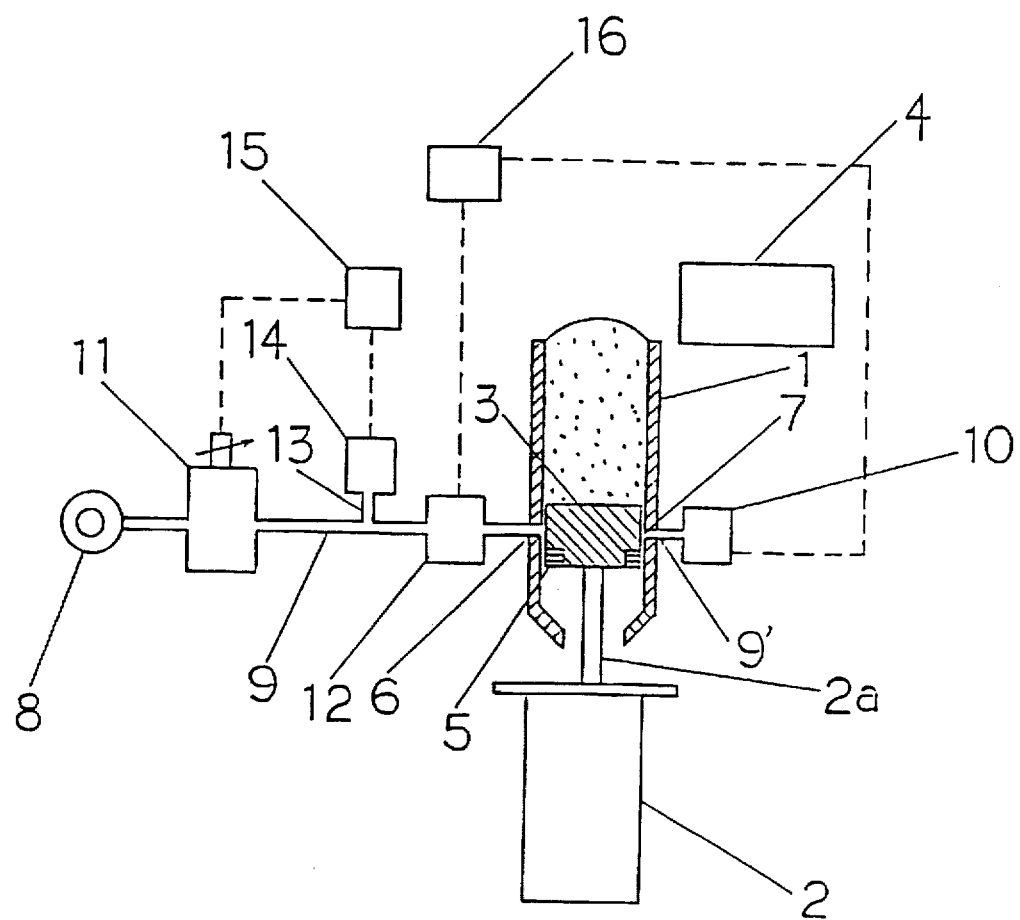
FIG. 2 is a schematic view of the device of FIG. 1 wherein molding sand is placed in the device.

To measure the air permeability of molding sand by the device configured as above, first the electric cylinder 2 is activated to raise the pressing body 3 connected to the end of the pressing rod 2a until the body 3 closes the apertures 6 and 7 to disconnect the communication between the inside and outside of the testing cylinder. Then, molding sand is supplied to the testing cylinder 1 from its upper open end by a device (not shown) such that the testing cylinder 1 is filled with molding sand (see FIG. 2). Since the apertures 6 and 7 are closed off by the pressing body 3, the sand cannot enter them. The squeezing head 4 is then moved horizontally to push and drop the extra sand stacked head the testing cylinder 1 and to close its upper open end. The electric cylinder 2 is then activated to raise the pressing body 3 and press and compact the molding sand by it under a pressure per a preset motor torque. When the pressure of the pressing body 3 and reaction from the compacted molding sand are at equilibrium, the height of the molding sand is measured by the encoder (not shown) and the data on it is stored in the processor 16. After the completion of the compaction of the molding sand, the electric cylinder 2 is activated to lower the pressing body 3 until the sealing 5 attached to the lower and circumferential part of the pressing body 3 contacts the lower inner wall of the testing cylinder 1. At the lower stop position of the pressing body 3 it is situated slightly below the apertures 6 and 7 (see FIG. 1). Then the compressed air is introduced from the source 8 into the testing cylinder 1 through the air take-in aperture 6. Since the lower open end of the testing cylinder 1 is closed, the compressed air introduced into the cylinder circulates through the compacted molding sand located above the air take-in aperture 6 and goes out of the testing cylinder 1. Based on the flow rate of this air as measured by the flow sensor 12, the air pressure measured by the first pressure sensor 10, and the stored data on the height of the compacted molding sand, its permeability is calculated. Although in the above embodiment the permeability is measured by introducing air of a constant flow rate into the testing cylinder by using the electro pneumatic operated proportional valve 11, second pressure sensor 14, and pneumatic-electro converter 15, instead of these devices a valve of a constant flow rate may be used to introduce a constant air flow into the testing cylinder.

As is clear from the foregoing description, since the structure of the apparatus of the present invention enables compressed air to be directly supplied to the compacted molding sand and the air to be circulated through the molding sand, the permeability of the molding sand is accurately measured. Further, since the element which causes the measuring error due to the clogging of sand is eliminated, a reliable measurement of air permeability is obtained.

What we claim is:

1. An apparatus for measuring air permeability of molding sand, said apparatus comprising:

a hollow testing cylinder having an open upper end, a tapered lower end having an inner surface, and a side wall having an inner diameter, wherein the side wall separates an interior region within the testing cylinder from an exterior region outside the testing cylinder, said testing cylinder extending vertically and having an air take-in aperture and a detecting aperture formed in said side wall, the lower end of said testing cylinder defining an open aperture having a diameter smaller than the inner diameter of the side wall;

a squeezing head horizontally movable to close said open upper end of the testing cylinder; and a press cylinder disposed below said test cylinder, the press cylinder including a rod and a press body connected to the rod such that the press body slides vertically in the testing cylinder, wherein the press body opens the air take-in aperture and the detecting aperture when said press body is in a lowered position at the tapered lower end closing the open aperture, wherein the press body allows the interior region to communicate with the exterior region when said press body is in the lowered position, wherein the press body can be in an upper position relative to the testing cylinder when said press body starts to press mold a quantity of the sand fed into the testing cylinder, and wherein the press body closes the air take-in aperture and the detecting aperture when said press body is in the upper position.

2. The apparatus of claim 1, wherein the press body includes a sealing member on the lower periphery thereof in a position such that the sealing member contacts the inner surface of the tapered lower end when said press body is located at said tapered lower end.

3. An apparatus for measuring the air permeability of molding sand fed into a testing cylinder, comprising:

a hollow testing cylinder having an open upper end, a tapered lower end having an inner surface, and a side wall having an inner diameter, wherein the side wall separates an interior region within the testing cylinder from an exterior region outside the testing cylinder, said testing cylinder extending vertically and having an air take-in aperture and a detecting aperture formed in said side wall, the lower end of said testing cylinder defining an open aperture having a diameter smaller than the inner diameter of the side wall;

a squeezing head horizontally movable to close said upper open end of the testing cylinder;

an air-supply source connected to said air take-in aperture;

a pressure gauge in fluid contact with said detecting aperture; and a press cylinder disposed below said testing cylinder, said press cylinder including a rod and a press body connected to said rod such that said press body slides vertically in the testing cylinder, wherein the press body opens the air take-in aperture and the detecting aperture when said press body is in a lowered position at the tapered lower end closing the open aperture, wherein the press body allows the interior region to communicate with the exterior region when said press body is in the lowered position, wherein the press body can be in an upper position relative to the testing cylinder when said press body starts to press mold a quantity of the sand fed into the testing cylinder, and wherein the press body closes the air take-in aperture and the detecting aperture when said press body is in the upper position.

4. The apparatus of claim 3, wherein the press body includes a sealing member on the lower periphery thereof in a position such that the sealing member contacts the inner surface of said tapered lower end when said press body is located at said tapered lower end.

* * * * *